United States Patent [19]

Herzig

[11] Patent Number: 5,189,206
[45] Date of Patent: Feb. 23, 1993

[54] PROCESS FOR THE PREPARATION OF AMINOBENZENESULFONIC ACIDS

[75] Inventor: Paul Herzig, Basel, Switzerland

[73] Assignee: Ciba-Geigy Corporation, Ardsley, N.Y.

[21] Appl. No.: 746,131

[22] Filed: Aug. 12, 1991

Related U.S. Application Data

[63] Continuation of Ser. No. 492,705, Mar. 13, 1990, abandoned.

[30] Foreign Application Priority Data

Mar. 16, 1989 [CH] Switzerland ............................ 979/89

[51] Int. Cl.$^5$ .................. C07C 309/30; C07C 309/46
[52] U.S. Cl. ........................................ 562/58; 562/73; 534/632; 534/638
[58] Field of Search .................................... 562/58, 73

[56] References Cited

U.S. PATENT DOCUMENTS

| | | | |
|---|---|---|---|
| 1,773,706 | 8/1930 | Henle et al. | 562/73 |
| 1,970,556 | 8/1934 | Carswell | 562/98 |
| 4,089,895 | 5/1978 | Jäger | 260/509 |
| 4,717,514 | 1/1988 | Blank et al. | 260/508 |

FOREIGN PATENT DOCUMENTS

| | | | |
|---|---|---|---|
| 53-102329 | 9/1978 | Japan | 534/638 |
| 285488 | 5/1929 | United Kingdom | 562/58 |

OTHER PUBLICATIONS

Allen et al, Chemical Abstracts, vol. 61, #12117g (1964).
Ando et al, Chemical Abstracts, vol. 73, #57061g (1970).
Filippychev, Chemical Abstracts, vol. 45, #2922-3 (1951).
Kisteneva et al, Chemical Abstracts, vol. 45, #5654-5 (1951).
Logemann et al, Chemical Abstracts, vol. 54, #14168-9 (1960).
Protto et al, Chemical Abstracts, vol. 53, #6245e (1959).
Spryskov et al, Chemical Abstracts, vol. 51, #12847d, h (1957).
Zdenek et al, Chemical Abstracts, vol. 62, #2740-1 (1965).
Japan 1975 pp. 1070-1075 (Abstract) vol. 99, 24019, 1983.

*Primary Examiner*—Robert W. Ramsuer
*Attorney, Agent, or Firm*—Kevin T. Mansfield; Edward McC. Roberts

[57] ABSTRACT

There is disclosed a process for the preparation of compounds of formula

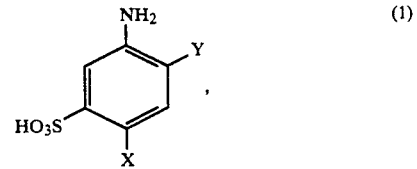

(1)

wherein the symbols are as defined in claim 1, which process comprises dissolving a compound of formula

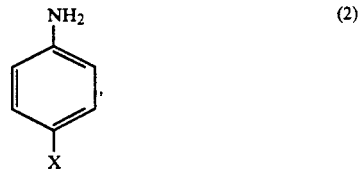

(2)

in sulfuric acid, adding this solution to oleum and reacting the mixture in the temperature range from 10° to 80° C. until a sulfo group has been completely introduced, and, in an optional further step, subjecting the reaction mixture to further reaction in the temperature range from 100° to 200° C. to introduce a second sulfo group.

The compounds of formula (1) obtainable by this process are useful intermediates for the synthesis of dyes and are particularly suitable diazo components for the synthesis of azo dyes.

10 Claims, No Drawings

PROCESS FOR THE PREPARATION OF AMINOBENZENESULFONIC ACIDS

This application is a continuation, of application Ser. No. 492,705, filed Mar. 13, 1990, now abandoned.

The present invention relates to a process for the preparation of aminobenzenemonosulfonic and aminobenzenedisulfonic acids which may be further substituted, and to the use of the aminobenzenesulfonic acids obtainable by said process for the synthesis of dyes.

A process for the preparation of 4-methylaniline-3-sulfonic acid, wherein p-toluidine is added to the 7-fold amount by weight of 20% oleum without additional solvent or diluent, is disclosed in J. Chem. Soc. of Japan 1975, pp. 1070–1075. The 4-methylaniline-3-sulfonic acid obtainable by this process is, however, very impure and contains a high proportion of unwanted 4-methylaniline-2-sulfonic acid, which then has to be removed by complicated procedures. To avoid such mixtures of isomers, the proposal is made in European patent application 0 149 460 to reverse the procedure by adding the oleum dropwise to the solution of p-toluidine in sulfuric acid. The ensuing reaction, however, is exothermic and requires complicated safety measures, for example an exact temperature control, to keep it under control. In addition, the batches have to be kept sufficiently small. Hence it is only possible to prepare 4-methylaniline-3-sulfonic acid in accordance with the process disclosed in European patent application 0 149 460 in a low space-time yield and using complicated apparatus.

There is consequently a need for a process which can be simply carried out in a large space-time yield and by means of which substituted aminobenzenemonosulfonic and aminobenzenedisulfonic acids can be prepared with the greatest possible selectivity. This need is met by the process of this invention.

Specifically, the present invention relates to a process for the preparation of compounds of formula

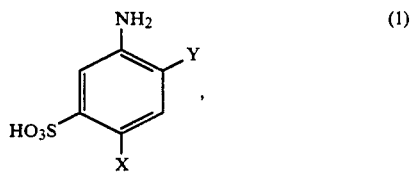

(1)

wherein X is halogen, hydroxy, unsubstituted or substituted $C_1$–$C_4$alkyl or unsubstituted or substituted $C_1$–$C_4$alkoxy, and Y is hydrogen or sulfo, which process comprises dissolving a compound of formula

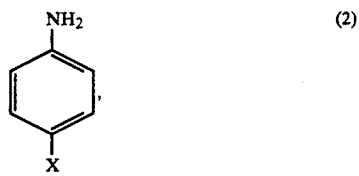

(2)

wherein X has the given meaning, in 1.5 to 10 mol of sulfuric acid per mol of compound of formula (2), adding this solution to enough oleum such that 2 to 4 mol of free $SO_3$ are present per mol of compound of formula (2), and reacting the mixture in the temperature range from 10° to 80° C. until a sulfo group has been completely introduced, and, in an optional further step, subjecting the reaction mixture to further reaction in the temperature range from 100° to 200° C. to introduce a second sulfo group.

X as halogen in the compounds of formulae (1) and (2) is typically fluoro, bromo or, preferably, chloro.

A $C_1$–$C_4$alkyl radical X will be generally understood as meaning in the context of this invention methyl, ethyl, n-propyl or isopropyl, or n-butyl, isobutyl, sec-butyl or tert-butyl. The alkyl radical X can in turn be substituted, for example by halogen, preferably chloro, or cyano; $C_1$–$C_4$alkoxy, typically methoxy, ethoxy, n-propoxy or isopropoxy, or n-butoxy, isobutoxy, sec-butoxy or tert-butoxy; $C_1$–$C_4$alkoxycarbonyl such as methoxycarbonyl or ethoxycarbonyl; carboxy; sulfamoyl; sulfo; or sulfato.

An alkyl radical X is preferably unsubstituted $C_1$–$C_2$alkyl and is most preferably methyl.

A $C_1$–$C_4$alkoxy radical X may carry one or more of the substituents mentioned above in connection with the alkyl radical. X as alkoxy is preferably unsubstituted $C_1$–$C_2$alkoxy and is most preferably methoxy.

Y in the compounds of formula (1) is preferably sulfo.

The process of this invention is particularly suitable for the preparation of compounds of formula (1) above, wherein X is chloro, methyl or ethyl, and Y is sulfo.

A particularly preferred embodiment of the process of this invention relates to the preparation of 4-methylaniline-2,5-disulfonic acid.

In the process of this invention, a solution of the compound of formula (2) in sulfuric acid is used, the amount of $H_2SO_4$ being 1.5 to 10 mol, preferably 1.5 to 5 mol and, most preferably, 1.5 to 3 mol, per mol of compound of formula (2). In general, 100% $H_2SO_4$ (sulfuric acid monohydrate) is used. However, it is also possible to use sulfuric acids of low water content, for example up to 8%, preferably up to 5%, of $H_2O$, based on the total amount of acid. This may, however, entail increasing the amount of oleum required for the sulfonation in the reactor in proportion to the water content of the $H_2SO_4$, as this water will naturally consume a portion of the $SO_3$ present in the oleum.

The addition of the compound of formula (2) to the sulfuric acid can be made in solid form, for example as powder, or preferably as melt. The temperature during this addition may vary within a wide range. A temperature range of, for example, 40° to 100° C., preferably of 50° to 85° C., has been found convenient. It has further been found useful to continue stirring for a few minutes after the addition of the compound of formula (2) so as to obtain a homogeneous, clear solution.

The oleum employed may be any conventional oleum. The oleum conveniently has an $SO_3$ content of, for example, 20 to 70% by weight and, preferably, of 60 to 66% by weight. The amount of oleum used in the process of this invention will be such that 2 to 4 mol, preferably 2 to 3 mol, of $SO_3$ are present per mol of compound of formula (2).

The temperature of the reaction mixture during the addition of the solution of the compound of formula (2) in sulfuric acid to the oleum is conveniently kept, for example, at 10° to 70° C., preferably from 15° to 55° C., with an ice bath. If desired, the temperature can also be varied within the given limits during the addition.

The time necessary for the addition of the solution of the compound of formula (2) in sulfuric acid to the oleum can vary within a wide range. A time from ca. 20 minutes to 5 hours, preferably from 30 minutes to 2.5 hours, has been found convenient.

When the addition of the compound of formula (2) to the oleum is complete, the reaction mixture can be subjected to a further reaction in the temperature range from, for example, 10° to 80° C., preferably from 15° to 75° C., in order to effect conversion of any unreacted compound of formula (2) still present in the reaction mixture. The presence of unreacted starting material can be detected, for example, by subjecting a sample of the reaction mixture to thin-layer chromatography. The time required for the further reaction may be from 10 minutes to 3 hours. However, the reaction is usually complete after ca. 15 to 30 minutes, so that no more starting compound of formula (2) is detectable in the reaction mixture.

The monosulfo compound of formula (1) obtained as described above [Y=hydrogen] can be further worked up as described hereinafter or, preferably, converted direct to the disulfo compound of formula (1) [Y=sulfo] by heating the reaction mixture to a temperature in the range from 100° to 200° C., preferably from 130° to 160° C., and allowing the reaction to continue at this temperature. The reaction time is conveniently, for example, from 1 to 10 hours, preferably from 1.5 to 5 hours and, most preferably, from 2.5 to 4 hours.

A particularly preferred embodiment of the present invention relates to a process for the preparation of 4-methylaniline-2,5-disulfonic acid, which comprises dissolving 4-methylaniline in 1.5 to 3 mol of sulfuric acid per mol of 4-methylaniline, adding this solution to enough 60–66% oleum that 2 to 3 mol of free $SO_3$ are present per mol of 4-methylaniline, and reacting the mixture for 10 minutes to 3 hours in the temperature range from 10° to 80° C., thereafter heating the reaction mixture to 130°–160° C. and reacting it further for 2.5 to 4 hours at this temperature.

The working up of the reaction mixture is effected in a manner known per se, for example by adding water or pouring the reaction mixture into water. Water itself or a mixture of water and ice or water in the form of crushed ice may be used for this purpose. Upon addition of water to the reaction mixture, the compound of formula (1) precipitates in the form of the free acid and can be isolated by conventional methods such as filtration or centrifugation.

It is furthermore also possible, and preferred, to isolate the compound of formula (1) in the form of the mono- or dialkali salt by first pouring the reaction mixture again into water or ice, then adding an excess of an alkali metal base such as lithium, sodium or potassium hydroxide, or lithium, sodium or potassium carbonate, or an alkali metal salt such as sodium sulfate or potassium sulfate, and isolating the precipitated alkali salt of the compound of formula (1) by filtration or centrifugation.

Compared with the process disclosed in European patent application 0 149 460, the process of this invention affords substantial advantages in respect of safety. Whereas in the former process a specific amount of oleum must first be added dropwise to the compound of formula (2) in order to get the reaction started at all, and the reaction then proceeds very turbulently and exothermically on account of the total amount of educt present, in the process of this invention the compound of formula (2), which is added dilute to the oleum, reacts quite spontaneously, i.e. the exothermic reaction can be controlled via the rate of addition of the compound of formula (2) and the process can thus be carried out in a greater space-time yield.

On the other hand, because of the spontaneous reaction of the compound of formula (2) with the oleum, and in the light of the disclosure of J. Chem. Soc. of Japan 1975, pp. 1070–1075, it must be regarded as surprising that the compounds of formula (1) are obtained by the process of this invention in very high purity. Thus the monosulfo compounds of formula (1) [Y=hydrogen] are obtained virtually free of starting compound of formula (2) and of troublesome isomer of formula

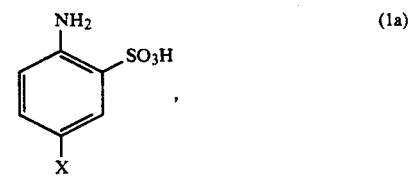

wherein X is as previously defined.

It is particularly surprising that also the disulfo compounds of formula (1) [Y=sulfo] are obtained in a purity of >97%, preferably of ≧99%. Almost no more troublesome isomer of formula

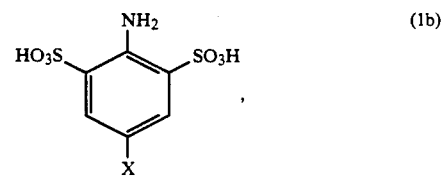

wherein X is as previously defined, can be detected in the reaction product by means of high-pressure liquid chromatography (HPLC).

The isolation of the compounds of formula (1) can therefore be effected without additional purification steps such as washing or recrystallisation.

Some of the compounds of formula (1) are novel. Accordingly, the invention also relates to compounds of formula (1) as indicated above wherein Y is sulfo and X is fluoro, chloro, bromo or $C_2$–$C_4$-alkyl.

The compounds of formula (1) obtainable by the process of this invention are useful intermediates, for example for the synthesis of dyes. They are particularly suitable diazo components for the synthesis of azo dyes.

A particularly preferred utility of the 4-methylaniline-2,5-disulfonic acid obtainable by the process of this invention is as diazo component for the synthesis of fiber-reactive azo dyes and, most particularly, for the synthesis of dyes of formula

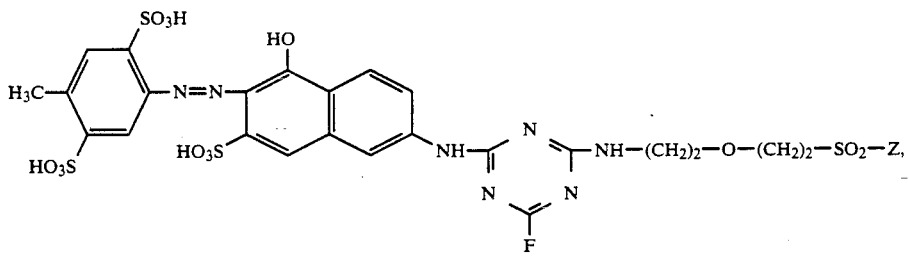

(3)

wherein Z is a radical —CH₂—CH₂—A or preferably vinyl, and A is —Cl, —OSO₃H, —SSO₃H, —OCOCH₃ or —OCO—C₆H₅.

The invention is illustrated by the following non-limitative Examples in which parts and percentages are by weight.

EXAMPLE 1

107 parts of fused p-toluidine are added dropwise at 50°-55° C. to 240 parts of 100% sulfuric acid. The mixture is stirred for 30 minutes and then the resultant solution is run into 320 parts of 66% oleum over 2 hours, while keeping the temperature at 15°-20° C. by cooling with ice. After a further 20 minutes, no more p-toluidine is detectable in the reaction mixture by HPLC.

The reaction mixture is then heated to 150° C. and stirred for 3 hours at this temperature. After cooling to 50° C., the reaction mixture is poured on to 900 parts of ice and 370 parts of a 50% solution of potassium hydroxide are added dropwise at 20°-30° C. to the resulting clear solution. The batch is then cooled to 5° C. and the precipitated product is isolated by filtration, affording 411 parts of moist 56% 4-methylaniline-2,5-disulfonic acid, corresponding to a yield of 86%, based on p-toluidine. The product has a purity of 99%.

EXAMPLE 2

The procedure of Example 1 is repeated, except that the sulfonation mixture is poured into 1000 parts of ice/water and the product is salted out with 290 parts of potassium sulfate. Filtration gives 414 parts of moist 60% 4-methylaniline-2,5-disulfonic acid, corresponding to a yield of 93%, based on p-toluidine. The product has a purity of 99.5%.

EXAMPLE 3

128 parts of p-chloroaniline are added, in portions, at a maximum temperature of 85° C. to 238 parts of 100% sulfuric acid. The mixture is then stirred for 15 minutes at 65° C. until a clear solution forms. This sulfuric acid solution is run into 420 parts of 66% oleum over 30 minutes, while keeping the temperature at 65°-70° C. by cooling with an ice bath. The reaction mixture is stirred for 2 hours at 70° C. to bring the reaction to completion and to give 4-chloroaniline-3-sulfonic acid. The batch is then heated to 160° C. and stirred for 3 hours at this temperature. After cooling to 50° C., the sulfonation mixture is poured into 1100 parts of ice/water, and the resulting clear solution is partially neutralised with 400 parts of a 50% solution of potassium hydroxide. The monopotassium salt of 4-chloroaniline-2,5-disulfonic acid slowly precipitates and is filtered with suction and dried under vacuum, affording 260 parts of 62.0% 4-chloroaniline-2,5-disulfonic acid, corresponding to a yield of 56%, based on p-chloroaniline. The purity is >97% (analysis by HPLC).

EXAMPLE 4

121 parts of 4-ethylaniline are added dropwise at 75°-83° C. to 183 parts of 100% sulfuric acid. The mixture is stirred for 15 minutes at 80° C., whereupon a clear solution forms. This sulfuric acid solution is added dropwise over 40 minutes to 320 parts of 66% oleum, while keeping the temperature at 60°-65° C. by cooling with an ice bath. After stirring for 15 minutes at 65° C., no more 4-ethylaniline can be detected. Stirring is continued for 4 hours at 150° C., then the sulfonation mixture is cooled to 80° C. and poured into 900 parts of ice/water. The monopotassium salt of 4-ethylaniline-2,5-disulfonic acid is precipitated by the dropwise addition of 370 parts of a 50% solution of potassium hydroxide and isolated by filtration, affording 350 parts of moist 53.0% 4-ethylaniline-2,5-disulfonic acid, corresponding to a yield of 66%, based on 4-ethylaniline. The purity is >99% (analysis by HPLC).

EXAMPLE 5

107 parts of fused p-toluidine are added dropwise over 30 minutes to 183 parts of 100% sulfuric acid, while keeping the temperature at 75°-80° C. After stirring for 15 minutes the p-toluidine is completely dissolved. This sulfuric acid solution is then run into 260 parts of 66% oleum over 30 minutes, while keeping the temperature at 40°-50° C. by cooling with an ice bath. Stirring is continued for 30 minutes at 45°-50° C., after which time no more educt can be detected by HPLC. The batch is poured into 500 parts of ice/water and the precipitated 4-methylaniline-3-sulfonic acid is filtered with suction and washed with 500 parts of ice/water, affording 248 parts of moist 70.0% 4-methylaniline-3-sulfonic acid, corresponding to a yield of 93%, based on p-toluidine. No more p-toluidine and no more 4-methylaniline-2-sulfonic acid is detectable by HPLC (<0.1%).

EXAMPLE 6

123 parts of fused p-anisidine are added dropwise over 30 minutes to 240 parts of 100% sulfuric acid, while keeping the temperature at 55°-60° C. After stirring for 15 minutes the p-anisidine is completely dissolved. This sulfuric acid solution is then run into 242 parts of 66% oleum over 30 minutes, while keeping the temperature at 30°-40° C. by cooling with an ice bath. Stirring is continued for 30 minutes at 40° C., after which time no more educt can be detected by HPLC. The batch is poured into 1000 parts of ice/water and the precipitated 4-methoxyaniline-3-sulfonic acid is filtered with suction and washed with 500 parts of ice/water, affording 179 parts of moist 97.0% 4-methoxyaniline-3-sulfonic acid, corresponding to a yield of 85%, based on

What is claimed is:

1. A process for the preparation of a compound of the formula

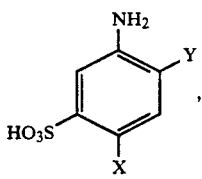
(1)

wherein X is chloro, $C_1$-$C_4$alkyl or $C_1$-$C_4$alkoxy and Y is hydrogen or sulfo, which process comprises dissolving a compound of the formula

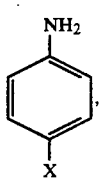
(2)

wherein X has the given meaning, in 1.5 to 10 moles of sulfuric acid per mole of compound of formula (2), adding this solution to enough oleum such that 2 to 4 moles of free $SO_3$ are present per mole of compound of formula (2), and reacting the mixture in the temperature range from 10° to 80° C. until a sulfo group has been completely introduced, and, if Y is sulfo, subjecting the reaction mixture to further reaction in the temperature range from 100° to 200° C. to introduce a second sulfo group.

2. A process according to claim 1 for the preparation of a compound of formula (1), wherein X is chloro, methyl or ethyl, and Y is sulfo.

3. A process according to claim 1 for the preparation of 4-methylaniline-2,5-disulfonic acid.

4. A process according to claim 1, which comprises using 1.5 to 5 mol of sulfuric acid per mol of compound of formula (2).

5. A process according to claim 1, which comprises using oleum having an $SO_3$ content of 60 to 66% by weight.

6. A process according to claim 1, wherein a further reaction is carried out in the temperature range from 130° to 160° C. to introduce a second sulfo group.

7. A process according to claim 1, wherein the isolation of the compound of formula (1) is effected without additional purification steps.

8. A process for the preparation of 4-methylaniline-2,5-disulfonic acid, which comprises dissolving 4-methylaniline in 1.5 to 3 mol of sulfuric acid per mol of 4-methylaniline, adding this solution to enough 60–66% oleum that 2 to 3 mol of free $SO_3$ are present per mol of 4-methylaniline, and reacting the mixture for 10 minutes to 3 hours in the temperature range from 10° to 80° C., thereafter heating the reaction mixture to 130°-160° C. and reacting it further for 2.5 to 4 hours at this temperature.

9. A process according to claim 8, wherein the 4-methylaniline-2,5-disulfonic acid is obtained in a purity of >97%.

10. A process according to claim 9, wherein the 4-methylaniline-2,5,-disulfonic acid is obtained in a purity of ≧99%.

* * * * *